United States Patent [19]

Dostert et al.

[11] 4,150,029
[45] Apr. 17, 1979

[54] 3-ARYL 2-OXAZOLIDINONES, THEIR PROCESS OF PREPARATION AND THEIR THERAPEUTICAL APPLICATION

[75] Inventors: Philippe L. Dostert, Chaville; Colette A. Douzon, Paris; Guy R. Bourgery, Colombes; Claude J. Gouret, Meudon; Gisele C. Mocquet, Paris; Jean A. Coston, Garches, all of France

[73] Assignee: Delalande S.A., Courbevoie, France

[21] Appl. No.: 771,814

[22] Filed: Feb. 23, 1977

[30] Foreign Application Priority Data

Mar. 1, 1976 [FR] France .................................. 76 05751
Jun. 28, 1976 [FR] France .................................. 76 19578

[51] Int. Cl.² ................................................ C07D 263/24
[52] U.S. Cl. ......................... 260/307 C; 260/326.5 L; 260/465 E; 260/573; 424/267; 424/272; 546/209
[58] Field of Search .................................. 260/307 C

[56] References Cited

U.S. PATENT DOCUMENTS 3,641,036  2/1972  Fauran et al. .................... 260/268 C
3,655,687  4/1972  Fauran et al. .................... 260/307 C

OTHER PUBLICATIONS

Fauran et al. (III)-C.A. 79, 105117c (1973).

*Primary Examiner*—Raymond V. Rush
*Attorney, Agent, or Firm*—Blanchard, Flynn, Thiel, Boutell & Tanis

[57] ABSTRACT

Compounds having the formula

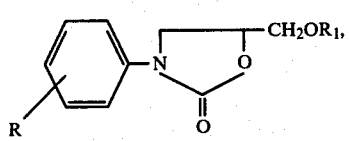

wherein $R_1$ is hydrogen or $CONHR_7$ and $R_7$ is methyl or isopropyl, and wherein
when $R_1$ is hydrogen: R is p-nitro, p-cyano; p-aldehydo; p-acetyl; m-ethyl; m-nitro; m-bromo; 3,4-dimethyl; m-$NH_2$; p-methylamino; p-dimethylamino; p-diethylamino; p-methylbenzylamino; p-pyrrolidino; p-piperidino; $SR_4$ in para position in which $R_4$ is alkyl having 1 to 4 carbon atoms or cyclohexyl; $OR_5$ is para position in which $R_5$ is alkyl having 2 to 7 carbon atoms, cyclohexyl, cyclohexylmethyl, acetylmethyl; cyanomethyl; alkene-2 yl having 3 to 5 carbon atoms, butene-3 yl, cyclohexene-1 methyl, propargyl, butyne-2 yl,

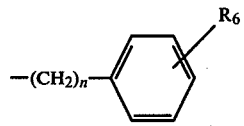

in which n is one or 2 and when n is one, $R_6$ is hydrogen, o-fluoro, o-methyl, m-chloro, m-fluoro, m-methyl, m-trifluoromethyl, p-chloro, p-bromo-, p-fluoro, p-cyano, p-nitro or p-dimethylamino and when n is 2, $R_6$ is hydrogen; and 3-methyl-4-benzyloxy:
  when $R_1$ is $CONHR_7$ and $R_7$ is methyl: R is m-trifluoromethyl; m-bromo; p-chloro; p-fluoro; 3,4-dichloro; p-thiomethyl; p-acetyl; $OR_8$ in para position wherein $R_8$ is alkyl having 2 to 5 carbon atoms, cyanomethyl, acetylmethyl, propargyl or

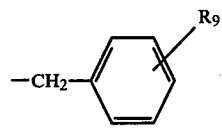

in which $R_9$ is hydrogen, m-chloro, m-bromo, m-fluoro, p-fluoro, p-chloro or p-nitro;
  and when $R_1$ is $CONHR_7$ and $R_7$ is isopropyl; R is m-trifluoromethyl or p-benzyloxy.

The compounds are prepared by cyclizing 1-phenylamino-2,3-propandiol derivatives to form 5-hydroxymethyl-3 phenyl-2-oxozolidinone derivatives. The 5-hydroxymethyl group can be transformed to —$CH_2OCONHR_7$ by reaction with methyl isocyanate or isopropyl isocyanate. The compounds possess psychotropic, particularly antidepressant, activity.

16 Claims, No Drawings

3-ARYL 2-OXAZOLIDINONES, THEIR PROCESS OF PREPARATION AND THEIR THERAPEUTICAL APPLICATION

The present invention relates to aryl-3-oxazolidinones-2, a process for preparing them and their application in therapeutics, particularly in the psychotopic field.

The compounds of the invention correspond more exactly to the following formula (I):

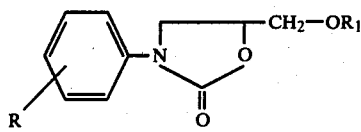

in which $R_1$ represents:
  either a hydrogen atom, in which case R may be:
    a p-nitro, p-cyano, p-aldehydo or p-acetyl radical;
    an m-ethyl, m-nitro, or m-bromo group; or two methyl groups in meta and para positions;
    an m-$NH_2$ group or

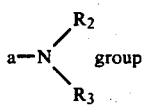

in the para position and in which the couple ($R_2$, $R_3$) can have the following meanings: (H, $CH_3$), ($CH_3$, $CH_3$), ($C_2H_5$, $C_2H_5$),

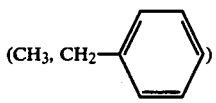

or form with the nitrogen atom to which they are bonded a pyrrolidino or piperidino radical;
a —$SR_4$ group in the para position and in which $R_4$ represents an alkyl radical having 1 to 4 carbon atoms or a cyclohexyl radical;
  a —$OR_5$ group in the para position and in which $R_5$ represents:
    an alkyl radical having 2 to 7 carbon atoms,
    a cyclohexyl, cyclohexylmethyl, acetylmethyl, or cyanomethyl radical,
    an alkene-2 yle radical having 3 to 5 carbon atoms, butene-3 yle or cyclohexene-1 methyl,
    a propargyl or butyne-2 yle radical,
    a radical of

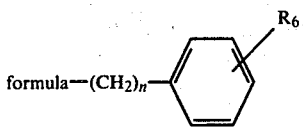

in which n is equal to 1 and $R_6$ represents a hydrogen atom, a fluorine atom or a methyl group when it is in the ortho position; a chlorine atom, a fluorine atom, a methyl or trifluoromethyl group when it is in the meta position; and a chlorine, bromine or fluorine atom, a cyano, nitro or dimethyl-amino group when it is in the para position; or n is equal to 2 and $R_6$ designates a hydrogen atom; or two groups, one methyl in the meta position, the other benzyloxy in the para position;
or a CO NH $R_7$ group where $R_7$ designates a methyl group in which case R may be:
  an m-trifluoromethyl or m-bromo group; a p-chloro or p-fluoro radical; two atoms of chlorine in meta and para positions; a p-thiomethyl or p-acetyl radical;
a —O $R_8$ group in the para position and in which $R_8$ designates:
  an alkyl radical having from 2 to 5 carbon atoms, a cyanomethyl or acetylmethyl radical, a propargyl radical, or
a radical of

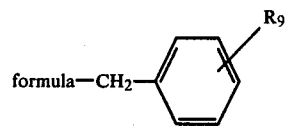

in which $R_9$ represents a hydrogen atom, a chlorine, bromine or fluorine atom when it is in the meta position, and a fluorine atom, a chlorine atom or a nitro group when it is in the para position;
or where $R_7$ designates an isopropyl group in which case R designates an m-trifluoromethyl or p-benzyloxy radical.

The process for preparing compounds of the invention of formula (I) in which $R_1$ is a hydrogen atom, consists in cyclizing, by ethyl carbonate action, a 1-phenylamino-2,3-propanediol of formula:

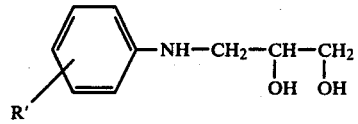

in which R' represents:
  a p-nitro, p-cyano, p-aldehydo- p-acetyl, m-methyl, m-nitro or m-bromo radical; or two methyl groups in meta and para positions;

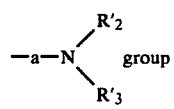

in para position and where the couple ($R'_2$, $R'_3$) can have the following meanings: ($CH_3$, $CH_3$), ($C_2H_5$, $C_2H_5$),

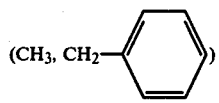

or form with the nitrogen atom to which they are bonded a pyrrolidino or piperidino radical;
  an S—$R_4$ group in the para position and where $R_4$ has the same meaning as in formula (I);
  a p-ethoxy or p-benzyloxy group; or
  two groups, one methyl in the meta position, the other benxyloxy in the para position,
which leads to compounds of formula:

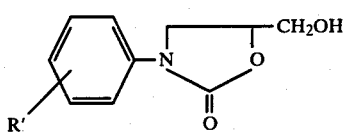

then possibly to subject the compound of formula (Ia): in which R' represents an m-nitro radical, to a catalytic reduction in an autoclave and in the presence of palladium on charcoal, which leads to the compound of formula:

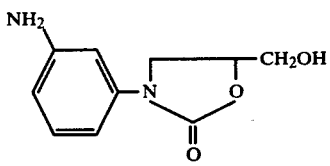

in which R' represents a p-N-methyl N-benzylamino group, to a hydrogenolysis action in alcohol in the presence of palladium on charcoal, which leads to the compound of formula:

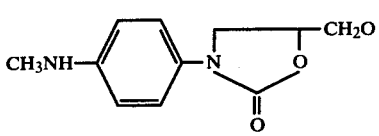

and
in which R' represents a p-benzyloxy group, to a hydrogenolysis action in alcohol in the presence of palladium on charcoal, which leads to the compound of formula:

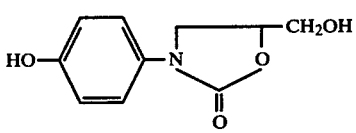

which is condensed with a product corresponding to one of the following formulas:

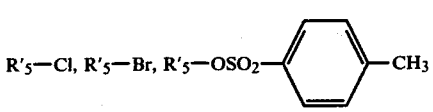

in which R'$_5$ has the same meaning as R$_5$ in formula I except for the ethyl and benzyl values, which leads to the compounds of formula:

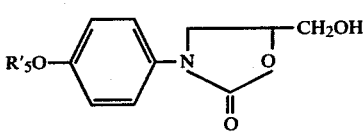

The compounds of formula II, in part novel, are, as to them, obtained by condensation, in methanol or ethanol, of anilines of formula:

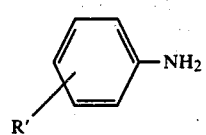

in which R' has the same meaning as in formula II, with glycidol of formula:

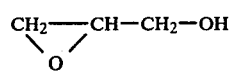

The compounds of formula (I) in which R$_1$ represents a CONHR$_7$ group where R$_7$ is a methyl or isopropyl group are, for their part, obtained by the action of an alkyl isocyanate of formula:

R'$_1$—N CO    (VI)

in which R'$_1$ designates a methyl or isopropyl group on an oxazolidinone of formula (I) in which R$_1$ represents a hydrogen atom and R can be:
an m-trifluoromethyl or m-bromo radical; a p-chloro or p-fluoro radical; two chlorine atoms in meta and para positions; a p-thiomethyl or p-acetyl radical; a —OR$_8$ group in the para position and in which R$_8$ designates:
an alkyl radical having 2 to 5 atoms of carbone, a cyanomethyl or acetylmethyl radical, a propargyl radical or a radical of

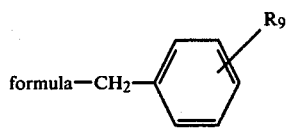

in which R$_9$ represents a hydrogen atom or a chlorine, bromine or fluorine atom when it is in the meta position, and a fluorine atom, a chlorine atom or a nitro group when it is in the para position.

The examples below are given solely as an illustration of the invention.

EXAMPLE 1: 3-ethylthiophenylamino 1,2-propanediol

Code No. 760465

A solution of 12.6 g (0.082 mole) of p-ethylthioaniline and 6.1 g (0.082 mole) of glycidol in 80 ml of ethanol is heated under reflux for 7 hours. Then, it is evaporated and the residue is chromatographed on silica (elution with a mixture of chloroform (80)-acetone(20)).
Yield: 43%
Melting point: <50° C.
Empirical formula: C$_{11}$H$_{17}$NO$_2$S
Elementary analysis:

|  | C | H | N |
|---|---|---|---|
| Calculated (%) | 58.12 | 7.54 | 6.16 |
| Obtained (%) | 57.96 | 7.45 | 6.30 |

EXAMPLE 2: 5-hydroxymethyl-3-metanitrophenyl-2 oxazolidinone

Code No. 740511

A mixture of 48 g (0.2 mole) of 3-metanitrophenylamino-1,2-propanediol (prepared according to a mode of operation similar to that of example 1), 200 ml of ethyl carbonate and 8 ml of triethylamine is heated at 100°–110° C. for 5 hours. The product obtained is filtered and recrystallised in absolute alcohol.
Melting point: 140° C.
Yield: 73%
Empirical formula: $C_{10}H_{10}N_2O_5$
Molecular weight: 238.20
Elementary analysis:

|  | C | H | N |
|---|---|---|---|
| Calculated (%) | 50.42 | 4.23 | 11.76 |
| Obtained (%) | 50.54 | 4.39 | 11.81 |

In the same way we can obtain compounds corresponding to the following code numbers and shown in table 1 below: 750341 - 750710 - 740564 - 740512 - 760271 - 760133 - 760311 - 760375 - 760474 - 760349 - 760082 - 760466 - 760483 - 760473 - 760600 - 760621 - 760037 - 770017 - 770054 - 760670 - 760167.

EXAMPLE 3: 5-hydroxymethyl 3-metaaminophenyl 2-oxazolidinone

Code No. 750079

A solution of 28 g (0.08 mole) of 5-hydroxymethyl 3-metanitrophenyl 2-oxazolidinone prepared in the previous example is hydrogenated, in an autoclave, under a pressure of 2 to 3 kg, at room temperature and in the presence of palladium on charcoal at 10%, in 400 ml of dioxane. The reaction is finished in 5 hours. Then it is filtered, the filtrate evaporated and the residue crystallised in alcohol.
Melting point: 118° C.
Yield: 10%
Empirical formula: $C_{10}H_{12}N_2O_3$
Molecular weight: 208.21
Elementary analysis:

|  | C | H | N |
|---|---|---|---|
| Calculated (%) | 57.68 | 5.81 | 13.46 |
| Obtained (%) | 57.39 | 5.77 | 13.22 |

EXAMPLE 4: 5-hydroxymethyl 3-p-N-methylaminophenyl 2-oxazolidinone

Code No. 760395

A solution of 19 g (0.061 mole) of 5-hydroxymethyl 3-p-N-benzyl N-methylaminophenyl 2-oxazolidinone, prepared according to a mode of operation similar to that of example 2, is hydrogenolysed in an autoclave at 50° C., under a pressure of 4 kg for 5 hours, in 400 ml of alcohol, in the presence of 0.6 ml of hydrochloric acid 6.4 N and 3 g of palladium on charcoal at 10%. It is filtered, the filtrate is evaporated, and the residue is taken up with an aqueous solution of bicarbonate of soda, then it is filtered and recrystallised in methanol.
Melting point: 174° C.
Yield: 6%
Empirical formula: $C_{11}H_{14}N_2O_3$ Elementary analysis:

|  | C | H | N |
|---|---|---|---|
| Calculated (%) | 59.45 | 6.35 | 12.61 |
| Obtained (%) | 59.29 | 6.39 | 12.61 |

EXAMPLE 5: 5-hydroxymethyl 3-p-cyanomethyloxyphenyl 2-oxazolidinone

Code No. 760651

1st step: 5-hydroxymethyl 3-p-hydroxyphenyl 2-oxazolidinone

Code No. 760172

A solution of 132.5 g (0.44 mole) of 5-hydroxymethyl 3-p-benzyloxyphenyl 2-oxazolidinone, prepared according to a mode of operation similar to that of example 2, is hydrogenolysed in an autoclave, between 45° and 50° C., under a pressure of 2 kg for 6 hours, in 1.5 litre of alcohol, in the presence of 13 g of palladium on charcoal at 10%. It is filtered, the filtrate is evaporated and recrystallised in isopropyl alcohol.
Melting point: 183° C.
Yield: 82%
Empirical formula: $C_{10}H_{11}NO_4$
Elementary analysis:

|  | C | H | N |
|---|---|---|---|
| Calculated (%) | 57.41 | 5.30 | 6.70 |
| Obtained (%) | 57.62 | 5.62 | 6.69 |

2nd step: 5-hydroxymethyl 3-p-cyanomethyloxyphenyl 2-oxazolidinone

Code No. 760651

A mixture of 15 g (0.07 mole) of 5-hydroxymethyl 3-p-hydroxyphenyl 2-oxazolidinone prepared in the previous step, 7.6 g (0.1 mole) of chloracetonitrile, 38 g (0.28 mole) of potassium carbonate and 1 g of potassium iodide is brought to reflux for 8 hours in 450 ml of acetone. It is filtered, the filtrate is evaporated and the residue crystallised in absolute alcohol.
Melting point: 98° C.
Yield: 67%
Empirical formula: $C_{12}H_{12}N_2O_4$
Molecular weight: 248.23
Elementary analysis:

|  | C | H | N |
|---|---|---|---|
| Calculated (%) | 58.06 | 4.87 | 11.29 |
| Obtained (%) | 57.91 | 4.92 | 11.21 |

In the same way, we can obtain the compounds corresponding to the following code numbers and listed in table I below: 760116 - 760303 - 760304 - 760414 - 760396 - 760549 - 760534 - 760314 - 770018 - 760306 - 760827 - 760650 - 760535 - 760536 - 760307 - 760877 - 770063 - 770104 - 760337 - 760317 - 760547 - 760556 - 760574 - 760548 - 760537 - 760533 - 760881 - 760622 - 760937 - 760432 - 760453 - 760652.

EXAMPLE 6: 5-N-methylcarbamoyloxymethyl 3-p-cyanomethyloxyphenyl 2-oxazolidinone

Code No. 760660

A solution of 7 g (0.028 mole) of 5-hydroxymethyl 3-p-cyanomethyloxyphenyl 2-oxazolidinone prepared in the 2nd step of example 5, and 4.8 g (0.084 mole) of methyl isocyanate in 30 ml of 1,2-dichlorethane is heated at 110° C. in a sealed tube for 3 hours. Then the solvent is evaporated, the residue crystallised in ether and recrystallised in methanol.
Melting point: 90° C.
Yield: 70%
Empirical formula: $C_{14}H_{15}N_3O_5$
Molecular weight: 305.28
Elementary analysis:

|  | C | H | N |
|---|---|---|---|
| Calculated (%) | 55.08 | 4.95 | 13.77 |
| Obtained (%) | 54.91 | 4.84 | 13.68 |

In the same way we can obtain the compounds corresponding to the following code numbers and listed in table I below: 740704 - 750479 - 750726 - 750685 - 750820 - 740711 - 760786 - 760104 - 760663 - 760662 - 760712 - 760819 - 760658 - 760729 - 760676 - 760717 - 760730 - 760409 - 760723 - 760728 - 760809 - 760733 - 760731.

Tables I and II below give respectively the compounds of formula (I) of the invention and new intermediate compounds (II), these later being prepared according to a mode of operation similar to that of example 1.

TABLE I

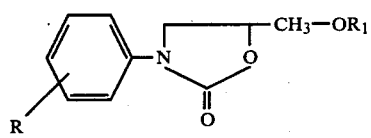

| Code Number | R | $R_1$ | Empirical formula | Molecular weight | Melting point (° C.) | Yield (%) | Calculated (%) C | H | N | Obtained (%) C | H | N |
|---|---|---|---|---|---|---|---|---|---|---|---|---|
| 740704 | 3CF₃ | CONH—CH₃ | $C_{13}H_{13}F_3N_2O_4$ | 318.25 | 115 | 75 | 49.06 | 4.12 | 8.80 | 48.79 | 3.95 | 8.61 |
| 750479 | 4Cl | " | $C_{12}H_{13}ClN_2O_4$ | 284.70 | 110 | 52 | 50.62 | 4.60 | 9.84 | 50.84 | 4.62 | 9.68 |
| 750726 | 3Br | " | $C_{12}H_{13}BrN_2O_4$ | 329.15 | 90 | 75 | 43.79 | 3.98 | 8.51 | 43.89 | 4.08 | 8.36 |
| 750685 | 4F | " | $C_{12}H_{13}FN_2O_4$ | 268.24 | 100 | 70 | 53.73 | 4.89 | 10.44 | 53.76 | 5.00 | 10.25 |
| 750820 | 3,4diCl | " | $C_{12}H_{12}Cl_2N_2O_4$ | 319.15 | 123 | 66 | 45.16 | 3.79 | 8.78 | 45.04 | 3.63 | 8.49 |
| 740711 | 3CF₃ | CONH—CH(CH₃)₂ | $C_{15}H_{17}F_3N_2O_4$ | 346.30 | 121 | 61 | 52.02 | 4.95 | 8.09 | 52.26 | 5.06 | 8.03 |
| 750341 | 3,4diCH₃ | H | $C_{12}H_{15}NO_3$ | 221.25 | 129 | 73 | 65.14 | 6.83 | 6.33 | 65.15 | 6.80 | 6.32 |
| 750710 | 3Br | H | $C_{10}H_{10}BrNO_3$ | 272.90 | 100 | 64 | 44.14 | 3.70 | 5.14 | 44.21 | 3.94 | 5.20 |
| 740564 | 4NO₂ | H | $C_{10}H_{10}N_2O_5$ | 238.20 | 154 | 68 | 50.42 | 4.23 | 11.76 | 50.42 | 4.26 | 11.59 |
| 740512 | 3C₂H₅ | H | $C_{12}H_{15}NO_3$ | 221.25 | 97 | 70 | 65.14 | 6.83 | 6.33 | 64.88 | 6.78 | 6.22 |
| 760271 | 4CN | " | $C_{11}H_{10}N_2O_3$ | 218.21 | 130 | 20 | 60.54 | 4.62 | 12.84 | 60.49 | 4.42 | 12.86 |
| 760133 | 4-N(CH₃)₂ | " | $C_{12}H_{16}N_2O_3$ | 236.26 | 150 | 25 | 61.00 | 6.83 | 11.86 | 60.72 | 7.07 | 11.77 |
| 760311 | 4-N(C₂H₅)₂ | " | $C_{14}H_{20}N_2O_3$ | 264.32 | 95 | 13 | 63.61 | 7.63 | 10.60 | 63.76 | 7.85 | 10.85 |
| 760375 | 4-N(CH₃)(CH₂C₆H₅) | " | $C_{18}H_{20}N_2O_3$ | 312 | 142 | 79 | 69.21 | 6.45 | 8.97 | 69.47 | 6.66 | 9.16 |
| 760474 | 4-N(pyrrolidinyl) | H | $C_{14}H_{18}N_2O_3$ | 262.30 | 168 | 42 | 64.10 | 6.92 | 10.68 | 63.92 | 6.59 | 10.91 |
| 760349 | 4-N(piperidinyl) | H | $C_{15}H_{20}N_2O_3$ | 276.33 | 170 | 39 | 65.19 | 7.30 | 10.14 | 64.89 | 7.27 | 10.44 |
| 760082 | 4 SCH₃ | H | $C_{11}H_{13}NO_3S$ | 239.29 | 133 | 62 | 55.21 | 5.48 | 5.85 | 54.95 | 5.38 | 5.92 |
| 760786 | 4 SCH₃ | CONH—CH₃ | $C_{13}H_{16}N_2O_4S$ | 296.34 | 120 | 78 | 52.69 | 5.44 | 9.45 | 52.59 | 5.23 | 9.60 |
| 760466 | 4 SC₂H₅ | H | $C_{12}H_{15}NO_3S$ | 253.31 | 110 | 66 | 56.89 | 5.97 | 5.53 | 56.82 | 5.85 | 5.48 |
| 760473 | 4 SC₄H₉(n) | H | $C_{14}H_{19}NO_3S$ | 281.37 | 106 | 52 | 59.76 | 6.81 | 4.98 | 59.76 | 6.59 | 4.81 |
| 760483 | 4 S—CH(CH₃)₂ | " | $C_{13}H_{17}NO_3S$ | 267.34 | 85 | 45 | 58.40 | 6.41 | 5.24 | 58.50 | 6.13 | 4.96 |
| 760600 | 4 SC₃H₇(n) | " | " | " | 102 | " | " | " | " | 58.68 | 6.58 | 5.20 |

TABLE I-continued

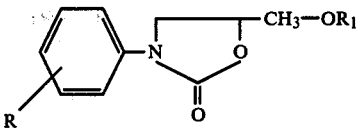

| Code Number | R | R₁ | Empirical formula | Molecular weight | Melting point (°C.) | Yield (%) | Calculated (%) C | H | N | Obtained (%) C | H | N |
|---|---|---|---|---|---|---|---|---|---|---|---|---|
| 760621 | 4 S—(cyclohexyl) | " | $C_{16}H_{21}NO_3S$ | 307.40 | 82 | 57 | 62.51 | 6.89 | 4.56 | 62.73 | 7.00 | 4.55 |
| 760037 | 4 OC₂H₅ | " | $C_{12}H_{15}NO_4$ | 237.25 | 133 | 91 | 60.75 | 6.37 | 5.90 | 60.81 | 6.54 | 5.89 |
| 760116 | 4 O—CH(CH₃)₂ | " | $C_{13}H_{17}NO_4$ | 251.27 | 74 | 56 | 62.14 | 6.82 | 5.57 | 62.29 | 6.77 | 5.48 |
| 760303 | 4 OC₃H₇(n) | " | " | " | 139 | 72 | " | " | " | 61.88 | 7.16 | 5.62 |
| 760304 | 4 OC₄H₉(n) | " | $C_{14}H_{19}NO_4$ | 265.30 | 122 | 68 | 63.38 | 7.22 | 5.28 | 63.53 | 7.21 | 5.37 |
| 760414 | 4O—CH₂—CH(CH₃)₂ | " | " | " | 110 | 30 | " | " | " | 63.41 | 7.25 | 5.19 |
| 760396 | 4 OC₅H₁₁(n) | " | $C_{15}H_{21}NO_4$ | 279.33 | 124 | 48 | 64.49 | 7.58 | 5.01 | 64.43 | 7.75 | 4.86 |
| 760549 | 4 OC₆H₁₃(n) | H | $C_{16}H_{23}NO_4$ | 293.35 | 115 | 76 | 65.50 | 7.90 | 4.78 | 65.55 | 8.00 | 4.50 |
| 760534 | 4 OC₇H₁₅(n) | " | $C_{17}H_{25}NO_4$ | 307.38 | 110 | 65 | 66.42 | 8.20 | 4.56 | 66.44 | 7.91 | 4.54 |
| 760314 | 4 O—(cyclohexyl) | " | $C_{16}H_{21}NO_4$ | 291.37 | 124 | 15 | 65.96 | 7.27 | 4.81 | 65.73 | 7.29 | 4.91 |
| 770018 | 4 O—C₄H₉(t) | " | $C_{14}H_{19}NO_4$ | 265.30 | 93 | 52 | 63.38 | 7.22 | 5.28 | 63.41 | 7.25 | 5.19 |
| 760104 | 4 OC₂H₅ | CONH—CH₃ | $C_{14}H_{18}N_2O_5$ | 294.30 | 110 | 52 | 57.13 | 6.16 | 9.52 | 57.02 | 6.22 | 9.51 |
| 760663 | 4 OC₃H₇(n) | " | $C_{15}H_{20}N_2O_5$ | 308.33 | 96 | 72 | 58.43 | 6.54 | 9.09 | 58.53 | 6.48 | 9.04 |
| 760662 | 4 OC₄H₉(n) | " | $C_{16}H_{22}N_2O_5$ | 322.35 | 84 | 80 | 59.61 | 6.88 | 8.69 | 59.60 | 6.91 | 8.66 |
| 760712 | 4 OC₄H₉(iso) | " | " | " | 89 | 88 | " | " | " | 59.33 | 6.87 | 8.61 |
| 760819 | 4 OC₅H₁₁(n) | CONH—CH₃ | $C_{17}H_{24}N_2O_5$ | 336.38 | 90 | 56 | 60.70 | 7.19 | 8.33 | 60.45 | 7.22 | 8.44 |
| 760306 | 4O—CH₂—CH=CH₂ | H | $C_{13}H_{15}NO_4$ | 249.26 | 109 | 76 | 62.64 | 6.07 | 5.62 | 62.69 | 6.14 | 5.68 |
| 760827 | 4O—CH₂—CH=CH—CH₃ (trans) | H | $C_{14}H_{17}NO_4$ | 263.28 | 150 | 62 | 63.86 | 6.51 | 5.32 | 63.74 | 6.52 | 5.31 |
| 760650 | 4O—CH₂—CH=C(CH₃)₂ | " | $C_{15}H_{19}NO_4$ | 277.31 | 100 | 34 | 64.96 | 6.91 | 5.05 | 64.77 | 6.97 | 4.87 |
| 760535 | 4O—CH₂—C(=CH₂)CH₃ | " | $C_{14}H_{17}NO_4$ | 263.28 | 82 | 74 | 63.86 | 6.51 | 5.32 | 64.09 | 6.57 | 5.22 |
| 760536 | 4 O—(CH₂)₂—CH=CH₂ | H | $C_{14}H_{17}NO_4$ | 263.28 | 116 | 18 | 63.86 | 6.51 | 5.32 | 63.97 | 6.81 | 5.55 |
| 760307 | 4 O—CH₂—C≡CH | " | $C_{13}H_{13}NO_4$ | 247.24 | 130 | 79 | 63.15 | 5.30 | 5.67 | 63.08 | 5.53 | 5.78 |
| 760658 | " | CONH—CH₃ | $C_{15}H_{16}N_2O_5$ | 304.29 | 122 | 71 | 59.20 | 5.30 | 9.21 | 58.95 | 5.43 | 9.31 |
| 760877 | 4 O—CH₂—C≡C—CH₃ | H | $C_{14}H_{15}NO_4$ | 261.27 | 140 | 58 | 64.36 | 5.79 | 5.36 | 63.98 | 5.80 | 5.18 |
| 770063 | 4 O—CH₂—(cyclohexenyl) | " | $C_{17}H_{21}NO_4$ | 303.35 | 99 | 45 | 67.31 | 6.98 | 4.62 | 67.41 | 6.97 | 4.78 |
| 770104 | 4 O—CH₂—(cyclohexyl) | " | $C_{17}H_{23}NO_4$ | 305.36 | 130 | 80 | 66.86 | 7.59 | 4.59 | 66.74 | 7.50 | 4.70 |
| 760167 | 4 O—CH₂—(phenyl) | " | $C_{17}H_{17}NO_4$ | 299.31 | 150 | 94 | 68.21 | 5.73 | 4.68 | 68.03 | 5.75 | 4.41 |
| 760337 | 4O—CH₂—(phenyl)-Cl | " | $C_{17}H_{16}ClNO_4$ | 333.76 | 152 | 66 | 61.17 | 4.83 | 4.20 | 60.98 | 4.70 | 4.44 |
| 760317 | 4O—(CH₂)₂—(phenyl) | " | $C_{18}H_{19}NO_4$ | 313.34 | 117 | 7 | 68.99 | 6.11 | 4.47 | 68.70 | 6.11 | 4.51 |
| 770017 | 4O—CH₂—(phenyl) 3CH₃ | H | $C_{18}H_{19}NO_4$ | 313.34 | 115 | 73 | 68.99 | 6.11 | 4.47 | 68.83 | 6.39 | 4.39 |
| 760547 | 4 O—CH₂—(phenyl)-F | " | $C_{17}H_{16}FNO_4$ | 317.31 | 147 | 84 | 64.34 | 5.08 | 4.41 | 64.20 | 4.91 | 4.17 |

TABLE I-continued

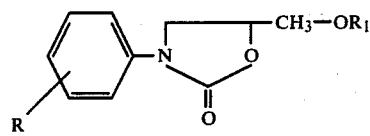

| Code Number | R | R$_1$ | Empirical formula | Molecular weight | Melting point (°C.) | Yield (%) | Calculated (%) C | H | N | Obtained (%) C | H | N |
|---|---|---|---|---|---|---|---|---|---|---|---|---|
| 760556 | 4O—CH$_2$—C$_6$H$_4$—CF$_3$ | " | C$_{18}$H$_{16}$F$_3$NO$_4$ | 367.32 | 89 | 59 | 58.85 | 4.39 | 3.81 | 58.63 | 4.31 | 3.82 |
| 760574 | 4O—CH$_2$—C$_6$H$_4$—Br | H | C$_{17}$H$_{16}$BrNO$_4$ | 378.21 | 153 | 75 | 53.98 | 4.26 | 3.70 | 53.81 | 4.17 | 3.46 |
| 760548 | 4O—CH$_2$—C$_6$H$_4$—Cl | " | C$_{17}$H$_{16}$ClNO$_4$ | " | 130 | 67 | " | " | " | 61.02 | 4.89 | 4.32 |
| 760729 | " | CONH—CH$_3$ | C$_{19}$H$_{19}$ClN$_2$O$_5$ | 390.82 | 109 | 71 | 58.39 | 4.90 | 7.17 | 58.33 | 4.89 | 7.10 |
| 760537 | 4O—CH$_2$—C$_6$H$_4$—CH$_3$ | H | C$_{18}$H$_{19}$NO$_4$ | 313.34 | 135 | 56 | 68.99 | 6.11 | 4.47 | 69.05 | 6.25 | 4.42 |
| 760533 | 4O—CH$_2$—C$_6$H$_4$—CH$_3$ | H | " | " | 123 | 62 | " | " | " | 69.20 | 6.37 | 4.60 |
| 760881 | 4O—CH$_2$—C$_6$H$_4$—CN | H | C$_{18}$H$_{16}$N$_2$O$_4$ | 324.32 | 159 | 76 | 66.66 | 4.97 | 8.64 | 66.62 | 4.95 | 8.71 |
| 760622 | 4O—CH$_2$—C$_6$H$_4$—NO$_2$ | H | C$_{17}$H$_{16}$N$_2$O$_6$ | 344.31 | 158 | 70 | 59.30 | 4.68 | 8.14 | 59.02 | 4.80 | 8.22 |
| 760676 | " | CONH—CH$_3$ | C$_{19}$H$_{19}$N$_3$O$_7$ | 401.36 | 153 | 89 | 56.85 | 4.77 | 10.47 | 56.64 | 4.63 | 10.53 |
| 760937 | 4 O—CH$_2$—C$_6$H$_4$—N(CH$_3$)$_2$ | H | C$_{19}$H$_{22}$N$_2$O$_4$ | 342.38 | 160 | 56 | 66.65 | 6.48 | 8.18 | 66.61 | 6.35 | 8.29 |
| 760432 | 4O—CH$_2$—C$_6$H$_4$—F | H | C$_{17}$H$_{16}$FNO$_4$ | 317.31 | 154 | 79 | 64.34 | 5.08 | 4.41 | 64.36 | 5.10 | 4.49 |
| 760717 | " | CONH—CH$_3$ | C$_{19}$H$_{19}$FN$_2$O$_5$ | 374.36 | 128 | 66 | 60.96 | 5.12 | 7.48 | 60.97 | 5.18 | 7.53 |
| 760453 | 4 O—CH$_2$—C$_6$H$_4$—F | H | C$_{16}$H$_{16}$FNO$_4$ | 317.31 | 141 | 81 | 64.34 | 5.08 | 4.41 | 64.60 | 5.01 | 4.33 |
| 760730 | " | CONH—CH$_3$ | C$_{19}$H$_{19}$FN$_2$O$_5$ | 374.36 | 112 | 50 | 60.96 | 5.12 | 7.48 | 60.99 | 5.19 | 7.77 |
| 760409 | 4 O—CH$_2$—C$_6$H$_5$ | CONH—CH$_3$ | C$_{19}$H$_{20}$N$_2$O$_5$ | 356.37 | 118 | 82 | 64.03 | 5.66 | 7.86 | 64.04 | 5.74 | 7.97 |
| 760723 | " | CONH—CH(CH$_3$)$_2$ | C$_{21}$H$_{24}$N$_2$O$_5$ | 384.42 | 132 | 83 | 65.61 | 6.29 | 7.29 | 65.91 | 6.83 | 7.12 |
| 760728 | 4O—CH$_2$—C$_6$H$_4$—Cl | CONH—CH$_3$ | C$_{19}$ClN$_2$O$_5$ | 390.81 | 148 | 68 | 58.39 | 4.90 | 7.17 | 58.38 | 5.08 | 6.92 |
| 760809 | 4O—CH$_2$—C$_6$H$_4$—Br | " | C$_{19}$H$_{19}$BrN$_2$O$_5$ | 435.27 | 109 | 54 | 52.43 | 4.40 | 6.44 | 52.58 | 4.41 | 6.51 |
| 760652 | 4 O—CH$_2$COOH$_3$ | H | C$_{13}$H$_{15}$NO$_5$ | 265.26 | 148 | 66 | 58.86 | 5.70 | 5.28 | 58.56 | 5.69 | 5.17 |
| 760733 | " | CONH—CH$_3$ | C$_{15}$H$_{18}$N$_2$O$_6$ | 322.31 | 102 | 62 | 55.89 | 5.63 | 8.69 | 55.63 | 5.76 | 8.60 |
| 770054 | 4 CHO | H | C$_{11}$H$_{11}$NO$_4$ | 219.20 | 123 | 35 | 59.72 | 5.01 | 6.33 | 59.49 | 4.66 | 6.20 |
| 760670 | 4 COCH$_3$ | H | C$_{12}$H$_{13}$NO$_4$ | 235.23 | 155 | 63 | 61.27 | 5.57 | 5.95 | 61.44 | 5.63 | 5.96 |
| 760731 | " | CONH—CH$_3$ | C$_{14}$H$_{16}$N$_2$O$_5$ | 292.28 | 130 | 49 | 57.53 | 5.52 | 9.59 | 57.23 | 5.27 | 9.43 |

TABLE II

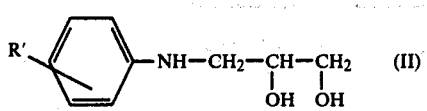

| Code Number | R | Empirical formula | Molecular weight | Melting point (° C.) | Yield (%) | Elementary analysis Calculated (%) C | H | N | Obtained (%) C | H | N |
|---|---|---|---|---|---|---|---|---|---|---|---|
| 760472 | 4-SC$_4$H$_9$(n) | C$_{13}$H$_{21}$NO$_2$S | 255.37 | <50 | 51 | 61.14 | 8.29 | 5.49 | 60.89 | 8.28 | 5.34 |
| 760498 | 4-SC$_3$H$_7$(iso) | C$_{12}$H$_{19}$NO$_2$S | 241.35 | *1 | 59 | 59.72 | 7.94 | 5.80 | 59.23 | 8.54 | 5.94 |
| 760599 | 4-SC$_3$H$_7$(n) | " | " | *2 | 48 | " | " | " | 59.60 | 8.25 | 5.48 |
| 760982 | 4-S-cyclohexyl | C$_{15}$H$_{23}$NO$_2$S | 281.41 | 82 | 63 | 64.02 | 8.24 | 4.98 | 63.86 | 8.42 | 4.98 |
| 760464 | 4-N-pyrrolidinyl | C$_{13}$H$_{20}$N$_2$O$_2$ | 236.31 | 125 | 20 | 66.07 | 8.53 | 11.86 | 65.78 | 8.49 | 12.02 |
| 760355 | 4-N-piperidinyl | C$_{14}$H$_{22}$N$_2$O$_2$ | 250.33 | 86 | 23 | 67.17 | 8.86 | 11.19 | 67.47 | 9.14 | 11.02 |
| 760732 | 4-CH$_3$CO— | C$_{11}$H$_{15}$NO$_3$ | 209.24 | 135 | 48 | 63.14 | 7.23 | 6.69 | 63.17 | 7.54 | 7.06 |

*1: Eb$_{0.04}$ = 250° C.
*2: Eb$_{0.01}$ = 250° C.

The compounds of formula (I) were studied on laboratory animals and showed activities in the psychotropic field, as potential antidepressants.

These activities show up in the following tests.

Test A

Potentiation in a mouse of generalised trembling caused by an intraperitoneal injection (200 mg/kg) of dl-5-hydroxytryptophane, according to the mode of operation described by GOURET C. and RAYNAUD G. in the J. Pharmacol. (PARIS), (1974), 5, 231.

Test B

Antagonism in relation to ptosis observed one hour after an intravenous injection (2 mg/kg) of reserpine was given to a mouse, according to the mode of operation described by GOURET C. and THOMAS J. in J. Pharmacol. (PARIS), (1973), 4, 401.

Test C

Diminution in the density of pontogeniculo-occipital points (P.G.O.) caused by injecting a cat with 0.5 mg/kg of reserpine, according to the mode of operation described by COSTON A. and GOURET C. in J. Pharmacol. (PARIS), (1976), 7, 409.

The results of these three tests as well as those of a reference substance TOLOXATONE are given in table III below:

TABLE III

| Tested compounds | Test A 50 DE (mg/kg/p.o.) | Test B 50 DE (mg/kg/p.o.) | Test C 50 DE (mg/kg/p.o.) |
|---|---|---|---|
| a/ According to the invention | | | |
| 740704 | 42 | 12 | 52 |
| 740512 | 68 | 32 | 50 |
| 750710 | 62 | 100 | 14 |
| 740711 | 19 | 26 | — |
| 750341 | 100 | 41 | 22 |
| 740564 | 38 | 42 | 16 |
| 740511 | 55 | 17 | 40 |
| 760271 | 20 | 11 | 11 |
| 760395 | 39 | 28 | 160 |
| 760133 | 11 | 7.2 | 4.5 |
| 760311 | 27 | 32 | 9 |
| 760375 | 39 | 28 | 160 |
| 760474 | 42 | 68 | 14 |
| 760082 | 22 | 18 | 8.4 |
| 760786 | >50 | 40 | 25.5 |
| 760466 | 40 | 32 | 8.25 |
| 760473 | 41 | 22 | 11.5 |
| 760600 | 19 | 15.4 | 6.26 |
| 760621 | 100 | 42 | 40 |
| 760037 | 16 | 40 | 5.4 |
| 760116 | 60 | 50 | 15 |
| 760303 | 9 | 14 | 6.9 |
| 760304 | 5 | 5 | 6.1 |
| 760414 | 13 | 3 | 5.5 |
| 760396 | 12 | 1.4 | 20 |
| 760549 | 26 | 11 | 85 |
| 760314 | 19 | 18 | 12 |
| 760104 | 48 | 44 | >50 |

TABLE III-continued

| Tested compounds | Test A 50 DE (mg/kg/p.o.) | Test B 50 DE (mg/kg/p.o.) | Test C 50 DE (mg/kg/p.o.) |
| --- | --- | --- | --- |
| 760662 | 48 | 17.5 | 23 |
| 760712 | 48 | 25 | 35 |
| 760306 | 14 | 29 | 2.5 |
| 760827 | 15 | 10 | 5.2 |
| 760650 | 25.5 | 3.4 | 7.03 |
| 760535 | 28 | 50 | 5.1 |
| 760536 | 8.6 | 15 | 6.3 |
| 760307 | 8 | 14 | 5 |
| 760658 | >12.5 | 27 | 13.9 |
| 760877 | 25 | 25 | 5.6 |
| 760167 | 9.5 | 3.3 | 15.2 |
| 760337 | 6 | 5 | 120 |
| 760317 | 25 | 17 | 45 |
| 760556 | 5 | 3.2 | 14.1 |
| 760574 | 21 | 22 | >50 |
| 760548 | 4.4 | 3.4 | 33.5 |
| 760729 | >12.5 | 23 | 50 |
| 760537 | 35 | 17 | 37.5 |
| 760533 | 41 | 54 | 51 |
| 760881 | 12.5 | 5 | 29 |
| 760622 | 5.5 | 2.1 | 40 |
| 760676 | >12.5 | 6.25 | 22 |
| 760432 | 3.8 | 2 | 24 |
| 760717 | >12.5 | 12.5 | >50 |
| 760453 | 5.5 | 7 | 11.6 |
| 760409 | 100 | 7 | >50 |
| 760723 | >50 | 17.5 | >50 |
| 760652 | 7.1 | 2.8 | 13 |
| 760651 | 5.5 | 2.5 | 1.5 |
| 760660 | >12.5 | 31 | 12.3 |
| 760670 | 21 | 10 | 14 |
| 760731 | >25 | 15 | 17.5 |
| b/ Reference | | | |
| TOLOXATONE | 60 | 50 | 28 |

As can be seen from the preceding results and those given in table IV below, the difference between lethal doses and active pharmacological doses is sufficient for the compounds of the invention to be used in therapeutics.

TABLE IV

| | Acute toxicity in mice | | |
| --- | --- | --- | --- |
| Tested compounds | Dose administered (mg/kg/p.o.) | Mortality (%) | 50 DL (mg/kg/p.o.) |
| a/ according to the invention | | | |
| 740704 | 2000 | 0 | — |
| 740711 | 1000 | 0 | — |
| 740564 | — | — | >1000 |
| 760271 | — | — | 1050 |
| 760082 | — | — | >2000 |
| 760037 | — | — | >2000 |
| 760304 | — | — | >2000 |
| 760167 | — | — | >2000 |
| b/ reference | | | |
| TOLOXATONE | — | — | 1850 |

As can be seen from the preceding tables the compounds of formula (I) have an activity superior or equal to that of the reference compound.

They are indicated in endogene and exogene depressive conditions, and will ge given orally in the form of tablets, pills, gelules with a dosage of 500 mg/day on average of active constituent.

What we claim is:

1. A compound having the formula

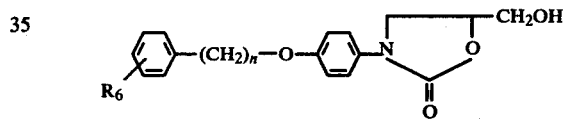

wherein n is 1 or 2; when n is 1, $R_6$ is H, o-F, o-$CH_3$, m-Cl, m-F, m-$CH_3$, m-$CF_3$, p-Cl, p-Br, p-F, p-CN, p-$NO_2$

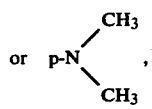

and when n is 2, $R_6$ is H.

2. A compound according to claim 1, having the formula

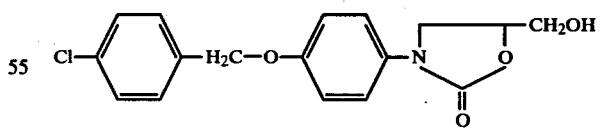

3. A compound according to claim 1, having the formula

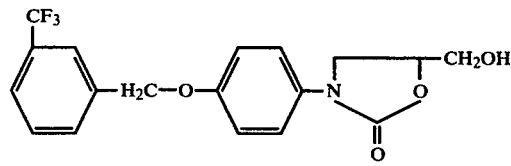

4. A compound according to claim 1, having the formula

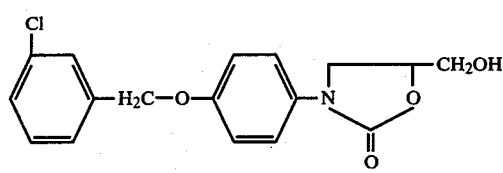

5. A compound according to claim 1, having the formula

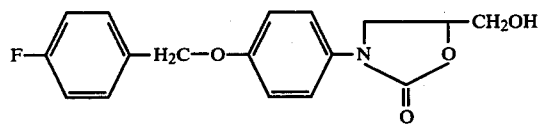

6. A compound according to claim 1, having the formula

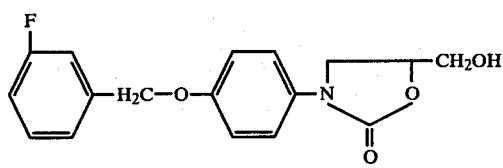

7. A compound having the formula

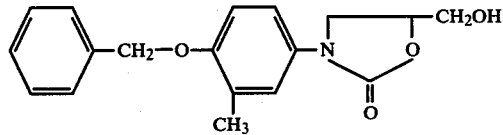

8. A compound having the formula

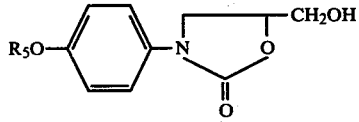

wherein $R_5$ is cyclohexyl, cyclohexylmethyl, acetylmethyl or cyanomethyl.

9. A compound according to claim 8, having the formula

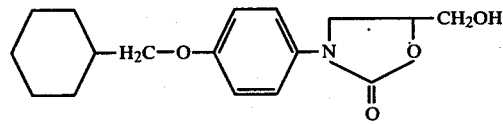

10. A compound having the formula

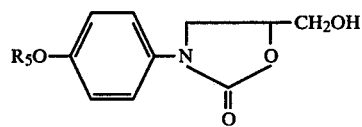

wherein $R_5$ is alkene-2-yl having 3 to 5 carbon atoms, butene-3-yl or cyclohexene-1 methyl.

11. A compound according to claim 10, having the formula

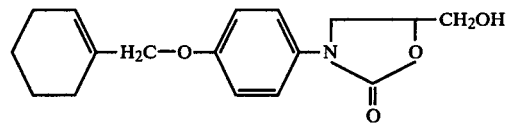

12. A compound having the formula

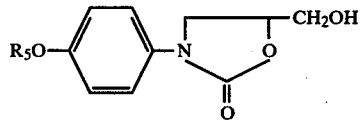

wherein $R_5$ is propargyl or butyne-2-yl.

13. A compound having the formula

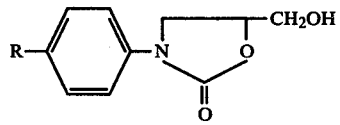

wherein R is selected from the group consisting of $OC_3H_7(n)$,

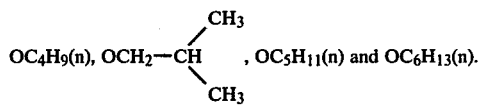

$OC_4H_9(n)$, $OCH_2-CH(CH_3)_2$, $OC_5H_{11}(n)$ and $OC_6H_{13}(n)$.

14. A compound having the formula

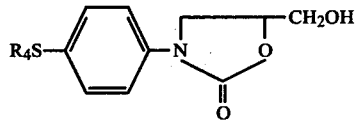

wherein $R_4$ is alkyl having 1 to 4 carbon atoms or cyclohexyl.

15. A compound having the formula

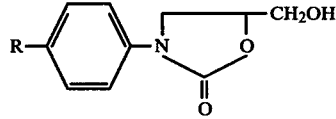

wherein R is —$NO_2$, —CN, —CHO or —$COCH_3$.

16. A compound having the formula

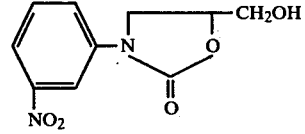

* * * * *